United States Patent
Batista et al.

(10) Patent No.: US 11,950,330 B2
(45) Date of Patent: *Apr. 2, 2024

(54) FLUID PERMEABLE HEATER ASSEMBLY FOR AN AEROSOL-GENERATING SYSTEM AND METHOD FOR ASSEMBLING A FLUID PERMEABLE HEATER FOR AN AEROSOL-GENERATING SYSTEM

(71) Applicant: Philip Morris Products S.A., Neuchatel (CH)

(72) Inventors: Rui Batista, Morges (CH); Jean-Marc Widmer, Lignieres (CH); Jens Ulrik Poulsen, Virum (DK)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/145,620

(22) Filed: Dec. 22, 2022

(65) Prior Publication Data

US 2023/0126886 A1    Apr. 27, 2023

Related U.S. Application Data

(63) Continuation of application No. 17/402,146, filed on Aug. 13, 2021, which is a continuation of application
(Continued)

(30) Foreign Application Priority Data

Feb. 10, 2014   (EP) ..................... 14154552
Feb. 10, 2014   (EP) ..................... 14154553
Feb. 10, 2014   (EP) ..................... 14154554

(51) Int. Cl.
*H05B 3/26*   (2006.01)
*A24B 15/16*  (2020.01)
(Continued)

(52) U.S. Cl.
CPC .............. *H05B 3/265* (2013.01); *A24B 15/16* (2013.01); *A24F 40/42* (2020.01); *A24F 40/46* (2020.01);
(Continued)

(58) Field of Classification Search
CPC .......... H05B 3/265; H05B 3/06; H05B 3/145; H05B 3/146; H05B 3/16; H05B 3/34;
(Continued)

(56) References Cited

U.S. PATENT DOCUMENTS

| 2,504,076 A | 4/1950 | Lindblom |
| 2,513,638 A | 7/1950 | Glabe |

(Continued)

FOREIGN PATENT DOCUMENTS

| AU | 67622/90 A | 6/1991 |
| CN | 101278599 | 10/2008 |

(Continued)

OTHER PUBLICATIONS

Extended European Search Report dated Jan. 2, 2023, in corresponding European Patent Application No. 22181571.5, 12 pages.
(Continued)

*Primary Examiner* — Shawntina T Fuqua
(74) *Attorney, Agent, or Firm* — Oblon, McClelland, Maier & Neustadt, L.L.P.

(57) ABSTRACT

A cartridge for an aerosol-generating system is provided, including a liquid storage portion including a housing containing a liquid aerosol-forming substrate, the housing having an open end; and a heater assembly including: an electrical heating element configured to heat the substrate to form an aerosol, the heating element including a planar filament arrangement having one or more electrically conductive filaments, an electrically insulating substrate having a planar attachment face, the filament arrangement disposed
(Continued)

on the planar attachment face, and clamping elements mechanically fixing the filament arrangement to the electrically insulating substrate and applying a pulling force onto the filament arrangement, at least a portion of the heater assembly being fluid-permeable, and the heater assembly being arranged over the open end of the housing.

20 Claims, 6 Drawing Sheets

Related U.S. Application Data

No. 16/190,317, filed on Nov. 14, 2018, now Pat. No. 11,153,937, which is a continuation of application No. 15/110,987, filed as application No. PCT/EP2014/077827 on Dec. 15, 2014, now Pat. No. 10,149,498.

(51) Int. Cl.
| | |
|---|---|
| *A24F 40/42* | (2020.01) |
| *A24F 40/46* | (2020.01) |
| *A24F 40/70* | (2020.01) |
| *A24F 42/80* | (2020.01) |
| *A61M 11/04* | (2006.01) |
| *A61M 15/06* | (2006.01) |
| *F22B 1/28* | (2006.01) |
| *G05D 23/24* | (2006.01) |
| *H05B 3/06* | (2006.01) |
| *H05B 3/14* | (2006.01) |
| *H05B 3/16* | (2006.01) |
| *H05B 3/34* | (2006.01) |
| *A24F 40/10* | (2020.01) |
| *A61M 15/00* | (2006.01) |
| *A61M 16/00* | (2006.01) |

(52) U.S. Cl.
CPC .............. *A24F 40/70* (2020.01); *A24F 42/80* (2020.01); *A61M 11/042* (2014.02); *A61M 15/06* (2013.01); *F22B 1/284* (2013.01); *G05D 23/2401* (2013.01); *H05B 3/06* (2013.01); *H05B 3/145* (2013.01); *H05B 3/146* (2013.01); *H05B 3/16* (2013.01); *H05B 3/34* (2013.01); *H05B 3/342* (2013.01); *H05B 3/347* (2013.01); *A24F 40/10* (2020.01); *A61M 15/0021* (2014.02); *A61M 15/0043* (2014.02); *A61M 2016/0024* (2013.01); *A61M 2205/3653* (2013.01); *A61M 2205/8206* (2013.01); *H05B 2203/011* (2013.01); *H05B 2203/013* (2013.01); *H05B 2203/014* (2013.01); *H05B 2203/015* (2013.01); *H05B 2203/017* (2013.01); *H05B 2203/021* (2013.01); *H05B 2203/022* (2013.01)

(58) Field of Classification Search
CPC .. H05B 3/342; H05B 3/347; H05B 2203/011; H05B 2203/013; H05B 2203/014; H05B 2203/015; H05B 2203/017; H05B 2203/021; H05B 2203/022; H05B 2203/016; A24B 15/16; A24F 40/42; A24F 40/46; A24F 40/70; A24F 40/10; A24F 42/80; A24F 47/008; A24F 47/00; A61M 11/042; A61M 15/06; A61M 15/0021; A61M 15/0043; A61M 2016/0024; A61M 2016/0021; A61M 2205/3653; A61M 2205/8206; A61M 2205/3368; A61M 2205/3633; A61M 2205/0211; A61M 2205/3673; A61M 2207/00; F22B 1/284; G05D 23/2401

See application file for complete search history.

(56) References Cited

U.S. PATENT DOCUMENTS

| | | |
|---|---|---|
| 5,095,921 A | 3/1992 | Losee |
| 6,181,874 B1 | 1/2001 | Ireland |
| 8,091,558 B2 | 1/2012 | Martzel |
| 8,641,139 B2 | 2/2014 | Gerken |
| 9,623,205 B2 | 4/2017 | Buchberger |
| 10,149,498 B2 | 12/2018 | Batista |
| 11,153,937 B2 | 10/2021 | Batista |
| 2007/0107879 A1 | 5/2007 | Radomski |
| 2008/0092912 A1 | 4/2008 | Robinson et al. |
| 2008/0110454 A1 | 5/2008 | White |
| 2009/0220222 A1 | 9/2009 | Rabin et al. |
| 2009/0272379 A1 | 11/2009 | Thorens |
| 2011/0022623 A1 | 1/2011 | Davis |
| 2011/0026580 A1 | 2/2011 | Deurenberg |
| 2011/0103780 A1 | 5/2011 | Gaulard |
| 2011/0226236 A1 | 9/2011 | Buchberger |
| 2011/0265806 A1 | 11/2011 | Alarcon |
| 2012/0026092 A1 | 2/2012 | Tsao |
| 2012/0153688 A1 | 6/2012 | Gerken |
| 2012/0260926 A1 | 10/2012 | Tu et al. |
| 2012/0260927 A1 | 10/2012 | Liu |
| 2013/0008716 A1 | 1/2013 | Kuittinen |
| 2013/0021341 A1 | 1/2013 | Choi |
| 2013/0081623 A1 | 4/2013 | Buchberger |
| 2013/0192618 A1 | 8/2013 | Li |
| 2013/0213419 A1 | 8/2013 | Tucker |
| 2013/0319407 A1 | 12/2013 | Liu |
| 2013/0333700 A1 | 12/2013 | Buchberger |
| 2014/0023842 A1 | 1/2014 | Urushiyama |
| 2014/0034668 A1 | 2/2014 | Carbone, II |
| 2014/0182610 A1 | 7/2014 | Liu |
| 2014/0305454 A1 | 10/2014 | Rinker et al. |
| 2015/0090279 A1 | 4/2015 | Chen |
| 2015/0101606 A1 | 4/2015 | White |
| 2015/0136156 A1 | 5/2015 | Liu |
| 2017/0258143 A1 | 9/2017 | Lederer |
| 2018/0020737 A1* | 1/2018 | Mironov ................... F16T 1/00 131/329 |
| 2018/0021997 A1 | 1/2018 | Widmer |
| 2021/0235759 A1* | 8/2021 | Courbat ................... A24F 40/46 |
| 2021/0401046 A1* | 12/2021 | Yamada ................... A24F 40/42 |
| 2022/0030950 A1* | 2/2022 | Taurino ................... A24F 40/42 |

FOREIGN PATENT DOCUMENTS

| | | |
|---|---|---|
| CN | 201767028 U | 3/2011 |
| CN | 102573968 A | 7/2012 |
| CN | 102861694 | 1/2013 |
| CN | 102939021 | 2/2013 |
| CN | 103431524 A | 12/2013 |
| CN | 103932401 A | 7/2014 |
| CN | 203986095 U | 12/2014 |
| CN | 203986096 U | 12/2014 |
| CN | 203986097 U | 12/2014 |
| CN | 204070542 U | 1/2015 |
| CN | 204317492 U | 5/2015 |
| DE | 20 2013 100 606 U1 | 4/2013 |
| EP | 0640297 | 3/1995 |
| EP | 2457411 | 5/2012 |
| EP | 2641490 | 9/2013 |
| GB | 2 422 083 A | 7/2006 |
| GB | 2504076 | 1/2014 |
| JP | H02124082 | 5/1990 |
| JP | 6-315366 | 11/1994 |
| JP | H1189551 | 4/1999 |
| JP | 11-512224 | 10/1999 |
| JP | 2013545474 | 12/2013 |
| JP | 54-78944 | 4/2014 |
| JP | 2017537634 A * | 12/2015 |
| JP | 2017/537634 A | 12/2017 |

(56) References Cited

FOREIGN PATENT DOCUMENTS

| | | | |
|---|---|---|---|
| KR | 2003-0017583 A | 3/2003 | |
| KR | 10-2014-0015253 | 2/2014 | |
| KZ | 28018 | 12/2013 | |
| RU | 2132629 C1 | 7/1999 | |
| RU | 2389419 C2 | 5/2010 | |
| WO | 2011/042212 | 4/2011 | |
| WO | WO 2011/109849 A1 | 9/2011 | |
| WO | 2011/137453 A2 | 11/2011 | |
| WO | 2011/146316 | 11/2011 | |
| WO | 2013/013808 | 1/2013 | |
| WO | 2013/045582 | 4/2013 | |
| WO | 2013/060743 | 5/2013 | |
| WO | 2013/083634 | 6/2013 | |
| WO | 2013/126777 | 8/2013 | |
| WO | 2013/149404 | 10/2013 | |
| WO | 2013/159245 A1 | 10/2013 | |
| WO | 2015/066127 A1 | 5/2015 | |
| WO | WO 2016/034157 A1 | 3/2016 | |
| WO | WO-2022155175 A1 * | 7/2022 | ............. A24F 40/20 |

OTHER PUBLICATIONS

The First Office Action dated May 8, 2021 in corresponding Chinese Patent Application No. 201910798851.8 (with English translation (9 pages).
Notice of Final Office Action dated Jun. 18, 2021 in corresponding Korean Patent Application No. 10-2016-7017843 (with English translation (14 pages).
U.S. Office Action dated Nov. 19, 2020 in corresponding U.S. Appl. No. 16/877,455. First Named Inventor: Rui Batista (13 pages).
PCT Search Report and Written Opinion for PCT/EP2014/077827 dated Mar. 26, 2015 (10 pages).
Office Action issued in Brazil for Application No. BR112016015685-4 dated Mar. 25, 2020 (7 pages).
Decision to Grant dated Nov. 18, 2021 in Russian Application No. 2018128584/07 (with Computer Generated English Translation)(reference AO cited therein).
Search Report dated Nov. 18, 2021 in Russian Application No. 2018128584/07 (with Computer Generated English Translation)( reference AO cited therein).
South Korean Office Action dated Jun. 27, 2022, in corresponding South Korean Patent Application No. 10-2022-7007562 (with English translation), citing document AO therein, 11 pages.
Notice of Allowance dated Dec. 26, 2022 in corresponding Korean Patent Application No. 10-2022-7007562 (with English Translation), 4 pages.
Notice of Opposition dated Apr. 26, 2023 in the corresponding European Patent Application No. 19161040.1, 24 pages.
"Crocodile clip". Wikipedia The Free Encyclopedia, Nov. 5, 2013, 3 pages.
"C-clamp", Wikipedia The Free Encyclopedia, This is an old revision of this page, as edited by 198.108.244.62 (talk) at 13:15, Feb. 5, 2014, 2 pages.
"Staple (fastener)", Wikipedia The Free Encyclopedia, This is an old revision of this page, as edited by Lawsonstu (talk/contribs) at 11:18, Jan. 4, 2014, 5 pages.
Korean Office Action dated Dec. 21, 2023 issued in Korean Patent Application No. 10-2023-7009955 filed on Dec. 15, 2014, with English Translation, total 6 pages.

* cited by examiner

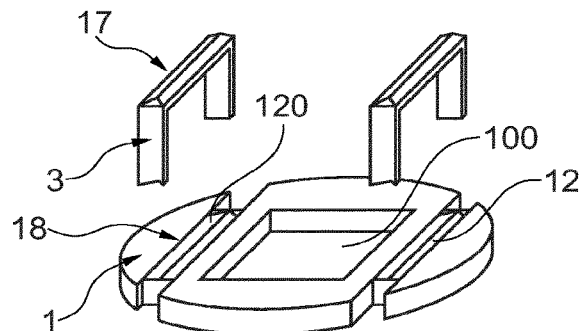
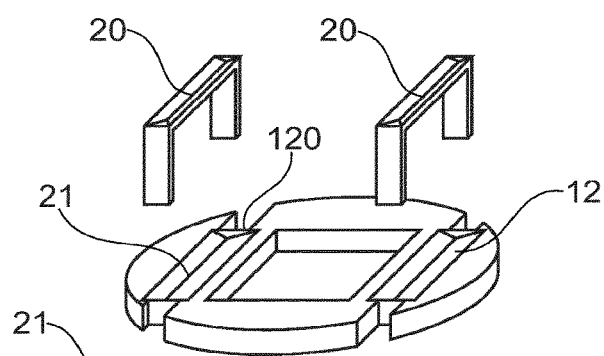
Fig. 7a
Fig. 8
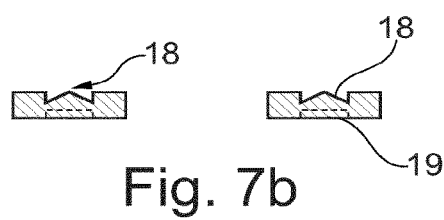
Fig. 7b
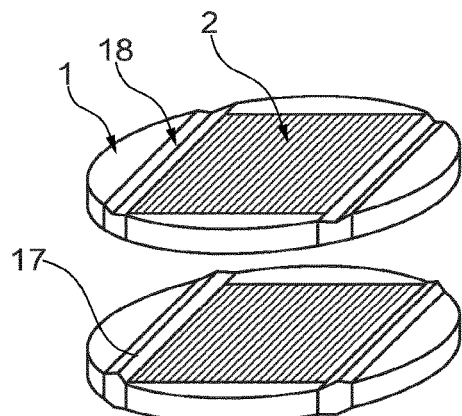
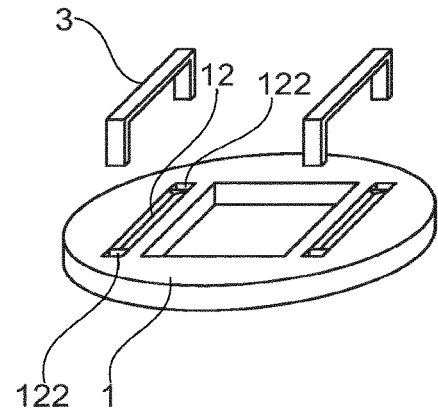
Fig. 9
Fig. 10

FLUID PERMEABLE HEATER ASSEMBLY FOR AN AEROSOL-GENERATING SYSTEM AND METHOD FOR ASSEMBLING A FLUID PERMEABLE HEATER FOR AN AEROSOL-GENERATING SYSTEM

CROSS-REFERENCE TO RELATED APPLICATIONS

This application is a continuation application of and claims benefit under 35 U.S.C. § 120 to U.S. application Ser. No. 17/402,146, filed on Aug. 13, 2021, which is a continuation application of and claims benefit under 35 U.S.C. § 120 to U.S. application Ser. No. 16/190,317, filed on Nov. 14, 2018 (now U.S. Pat. No. 11,153,937), which is a continuation application of and claims benefit under 35 U.S.C. § 120 to U.S. application Ser. No. 15/110,987, filed on Jul. 12, 2016 (now U.S. Pat. No. 10,149,498), which is a U.S. National Stage application of PCT/EP2014/077827, filed on Dec. 15, 2014, and claims benefit of priority under 35 U.S.C. § 119 to EP Application Nos. 14154554.1, 14154553.3, and 14154552.5, each filed on Feb. 10, 2014, the entire contents of each of which are incorporated herein by reference.

The invention relates to a fluid permeable heater assembly for aerosol-generating systems and a method for assembling a fluid permeable heater. Especially, the invention relates to a fluid permeable heater assembly for handheld aerosol-generating systems, such as electrically operated smoking systems.

Some aerosol-generating systems such as electrically operated smoking devices may comprise a battery and control electronics, a cartridge comprising a supply of aerosol forming substrate and an electrically operated vaporizer. A substance is vaporized from the aerosol forming substrate, for example by a heating element. The heating element may be an at least partially fluid permeable heater, for example a flat coil embedded in a ceramic material. However, such heaters are expensive in manufacture.

There is a need for a fluid permeable heater assembly for aerosol-generating systems, which is inexpensive to produce and is simple in manufacture. There is also need for an according method for assembling fluid permeable heaters.

According to a first aspect of the invention, there is provided a fluid permeable heater assembly for aerosol-generating systems, preferably electrically operated smoking systems. The fluid permeable heater assembly comprises a substrate, preferably an electrically insulating substrate. The substrate comprises an opening extending through the substrate. The heater assembly further comprises an electrically conductive substantially flat filament arrangement arranged over the opening in the substrate. The filament arrangement is mechanically fixed to the substrate with clamping means. The clamping means are also electrically conductive and serve as electrical contacts for providing a heating current through the filament arrangement as well as for stabilizing the filament arrangement clamped to the substrate.

Preferably, the heater assembly is assembled by mechanical means only. A fixation of the filament arrangement and substrate to each other, as well as electrical contact between filament arrangement and a contact for an external power source, for example a battery, is done by mechanical clamping. The clamping means provide for a secure fixation of the filament arrangement and for a reliable contact between the filament arrangement and the clamping means. Due to the mechanical clamping and establishing of the electrical contacting of the filament arrangement by mechanical means, no soldering, welding or etching of electrical contacts is required. This may facilitate manufacture and reduce costs of manufacturing parts of the heater assembly. Further this may also facilitate machinability of the heater assembly or of parts thereof. In addition, the mechanical fixation may improve reliability of the heater assembly by avoiding common issues of soldering and welding such as cold solder joints or cold welds. These are known for low strength, for failure under stress and for unreliable resistance. In addition, the filament arrangement does not come into direct contact with connectors of a battery of an aerosol-generating system, thus avoiding tearing of the filament arrangement upon insertion of the heater into the system.

With the method for assembling such a fluid permeable heater according to the invention three purposes may be combined in one single economic means: fixation of the filament arrangement to the substrate, stabilizing the filament arrangement in a plane and providing an electrical connector to a power source, for example an e-cigarette battery. The clamping means, corresponding clamping mechanism of a filament arrangement to a substrate and a corresponding assembling process is cost effective, industrially proof, functionally efficient, robust and compatible with a relatively small surface of a heater assembly.

The term "substantially flat" filament arrangement is used throughout the specification to refer to a filament arrangement that is in the form of a substantially two dimensional topological manifold. Thus, the substantially flat filament arrangement extends in two dimensions along a surface substantially more than in a third dimension. In particular, the dimensions of the substantially flat filament arrangement in the two dimensions within the surface is at least 5 times larger than in the third dimension, normal to the surface. An example of a substantially flat filament arrangement is a structure between two substantially parallel imaginary surfaces, wherein the distance between these two imaginary surfaces is substantially smaller than the extension within the surfaces. In some embodiments, the substantially flat filament arrangement is planar. In other embodiments, the substantially flat filament arrangement is curved along one or more dimensions, for example forming a dome shape or bridge shape.

The term "filament" is used throughout the specification to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The term "filament arrangement" is used throughout the specification to refer to an arrangement of one or preferably a plurality of filaments. The filament arrangement may be an array of filaments, for example arranged parallel to each other. Preferably, the filaments may form a mesh. The mesh may be woven or non-woven. Preferably, the filament arrangement has a thickness of between about 0.5 micrometers and 500 micrometers.

As a general rule, whenever the term "about" is used in connection with a particular value throughout this application this is to be understood such that the value following the term "about" does not have to be exactly the particular value due to technical considerations. However, the term "about" used in connection with a particular value is always to be understood to include and also to explicitly disclose the particular value following the term "about".

For example, the shape of a substrate and filament arrangement clamped to the substrate may be adapted to the shape of an end of a cartridge containing the aerosol-forming substance. Such an end of a cartridge may be planar but may also be curved, for example have a convex shape.

The opening in the substrate may substantially have any shape. Preferably, the opening has a simple shape easy to manufacture such as for example a circular, oval or rectangular shape, that is, a cylinder having a circular, oval or rectangular base extending through the substrate. Preferably, the opening in the substrate includes at least a central portion of the substrate. The central portion includes the fictive center of gravity of the substrate. Alternatively, or in addition, the central portion may comprise a longitudinal axis, for example a rotational axis, like, for example, the rotational axis of a circular disc shaped substrate.

The substantially flat filament arrangement is arranged over at least a portion of the opening by the clamping means. The substrate comprises an attachment face, where the substantially flat filament arrangement is positioned against in the mounted state. Preferably, the attachment face is a portion of the top surface of the substrate. The attachment face may include the opening as well as portions of the top surface of the substrate adjacent the opening. Preferably, the attachment face is planar. The clamping means apply a pulling force onto the filament arrangement. This pulling force is directed into at least a direction coplanar to the attachment face. Preferably, the pulling force is applied to the filament arrangement during assembly of the heater and preferably in the mounted state of the filament arrangement. The pulling force supports the planar arrangement of the filament arrangement and helps to stabilize the filament arrangement in the plane of the substrate. Preferably, the clamping means provide opposite pulling forces to the filament arrangement, stretching and stabilizing the filament arrangement in a plane.

The clamping means may comprise several separately arranged clamping elements, preferably two separately arranged clamping elements. Preferably, the separate clamping elements do not directly contact each other such that the separate elements form two contacts for applying power to the heater and heating the filament arrangement. More than one clamping element may serve as one electrical contact for the filament arrangement. More than one clamping element may serve as second electrical contact for the filament arrangement. Preferably, the clamping means are two electrically conductive clamping elements, preferably having shapes of clamps, clips or staples. Preferably, clamping means provide a clamping action along a line, thus preventing filament damage or tearing due to single point fixing. Preferably, the two clamping elements are arranged opposite each other, for example on opposite lateral sides of the substrate. Preferably, the heater assembly comprises few components, like for example, only a substrate, a filament arrangement and two clamping elements. A clamping means may also comprise a shape adapted to the form of an external connector for simplifying a connection and improving an external electrical contact.

Fluid permeable heater assemblies are suitable for vaporizing liquids of different kind of cartridges. For example, as an aerosol-forming substrate, a cartridge may contain a liquid or a liquid containing transport material such as for example a capillary material. Such a transport material and capillary material actively conveys liquid and is preferably oriented in the cartridge to convey liquid to the heater assembly. The filament arrangement is arranged close to the liquid or to the liquid containing capillary material such that heat produced by the filament arrangement may vaporize the liquid. Preferably, filament arrangement and aerosol-forming substrate are arranged such that liquid may flow into interstices of the filament arrangement by capillary action. The filament arrangement may also be in physical contact with a capillary material.

The electrically conductive filaments may define interstices between the filaments and the interstices may have a width of between 10 micrometers and 100 micrometers. Preferably the filaments give rise to capillary action in the interstices, so that in use, liquid to be vaporised is drawn into the interstices, increasing the contact area between the heater assembly and the liquid. The electrically conductive filaments may form a mesh of sizes between 160 Mesh US and 600 Mesh US (plus or minus 10 percent (that is between 160 and 600 filaments per inch (plus or minus 10 percent)). The width of the interstices is preferably between 75 micrometers and 25 micrometers.

The percentage of open area of a mesh, which is the ratio of the area of the interstices to the total area of the mesh is preferably between 25 and 60 percent. The mesh may be formed using different types of weave or lattice structures.

The filament arrangement may also be characterised by its ability to retain liquid, as is well understood in the art.

The electrically conductive filaments may have a diameter of between 10 micrometers and 100 micrometers, preferably between 8 micrometers and 50 micrometers, and more preferably between 8 micrometers and 40 micrometers. The area of the filament arrangement may be small, preferably less than or equal to 25 square millimeter, allowing it to be incorporated into a handheld system. The filament arrangement may, for example, be rectangular and have dimensions of 5 millimeter by 2 millimeter in the mounted state. Preferably, a filament arrangement covers an area of between 10 percent and 50 percent of the area of the heater assembly. More preferably, the filament arrangement covers an area of between 15 and 25 percent of the area of the heater assembly.

The filament arrangement may be formed by etching a sheet material, such as a foil. This may be particularly advantageous when the heater assembly comprises an array of parallel filaments. If the heater assembly comprises a mesh, the filaments may be individually formed and knitted or waved together.

The filaments of the heater assembly may be formed from any material with suitable electrical properties. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium-, titanium-, zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. Preferred materials for the electrically conductive filaments are 304, 316, 304L, 315L stainless steel, and graphite.

The electrical resistance of the filament arrangement is preferably between 0.3 Ohms and 4 Ohms. More preferably, the electrical resistance of the filament arrangement is between 0.5 Ohms and 3 Ohms, and more preferably about 1 Ohm. The electrical resistance of the filament arrangement is preferably at least an order of magnitude, and more preferably at least two orders of magnitude, greater than the electrical resistance of the contact portions. This ensures that the heat generated by passing current through the heater assembly is localised to the filament arrangement. It is advantageous to have a low overall resistance for the heater assembly if a system is powered by a battery. A low resistance, high current system allows for the delivery of high power to the heater element. This allows the heater element to heat the electrically conductive filament arrangement to a desired temperature quickly.

The heater assembly may comprise at least one filament made from a first material and at least one filament made from a second material different from the first material. This may be beneficial for electrical or mechanical reasons. For example, one or more of the filaments may be formed from a material having a resistance that varies significantly with temperature, such as for example an iron aluminium alloy. This allows a measure of resistance of the filaments to be used to determine temperature or changes in temperature. This can be used in a puff detection system. Alternatively, or in addition, this can be used for controlling the heater temperature to keep it within a desired temperature range. Sudden changes in temperature may also be used as a means to detect changes in air flow past the heater assembly resulting from a user puffing on an electrically operated smoking system. A preferred embodiment of this kind of filament material is, for example, an array of parallel filaments of a first material arranged above an array of parallel filaments of a second material, the arrays rotated versus each other forming a mesh. A combination of materials may also be used to improve the control of the resistance of the substantially flat filament arrangement. For example, materials with a high intrinsic resistance may be combined with materials with a low intrinsic resistance. This may be advantageous if one of the materials is more beneficial from other perspectives, for example price, machinability or other physical and chemical parameters. For example, one of the materials may be stainless steel.

Preferably, the substrate of the heater assembly is electrically insulating. The electrically insulating substrate may comprise any suitable material, and is preferably a material that is able to tolerate high temperatures (in excess of 300 degree Celsius) and rapid temperature changes. An example of a suitable material is a polyimide film, such as Kapton®, Polyetheretherketone (PEEK) or a ceramics material, preferably an open pored electrically insulating ceramic material. Preferably, the material of the substrate is non-brittle. The substrate material may have capillary action for liquid to be vaporized.

Preferably, the substrate is substantially flat. Preferably, the substrate is a disc, wherein the disc may be, for example, circular, oval or rectangular. The disc may be planar or curved. Preferably, the substrate also comprises a planar attachment face to be arranged facing a cartridge containing the aerosol-forming substrate such that the heater assembly and the cartridge, or a cover of the cartridge, respectively, have a planar contact surface. This allows for a flush arrangement of cartridge and heater assembly.

According to an aspect of the fluid permeable heater assembly according to the invention, the clamping means mechanically fixing the filament arrangement to the substrate provide a form-fit closure or a force-fit closure with the substrate. Form-fit and force-fit closures are two types of mechanical fixing, which are simple and secure for mechanically fixing components to each other. The two types of closure may be combined. In a form-fit closure, the clamping means and the substrate comprise corresponding forms. A fixation may be mainly or solely due to frictional forces between the interface of clamping means and substrate in a contact area. However, a form-fit closure may also be achieved, for example, by an enveloping of filament and substrate by the clamping means. In a force-fit closure, clamping means or substrate or both, clamping means and substrate, may comprise resilient portions, for example flexible legs or spring-like elements. The force applied by the clamping means or parts of the clamping means keep the filament arrangement affixed to the substrate.

Force-fit and form-fit closure may also be combined in a clamping mechanism of clamping means and substrate. For example a clamping means may contain parts made of a resilient material. Alternatively, or in addition, the clamping means may comprise a form that deviates from the form of a corresponding portion in the substrate. For example, a conically formed leg of a clamping means may be inserted into a recess in the substrate, wherein the recess has parallel inner walls.

According to another aspect of the fluid permeable heater assembly according to the invention, the clamping means extend over a portion of a lateral side of the substrate and comprise resilient leg portions. The resilient leg portions press the filament arrangement to a top surface of the substrate. Therein, filament arrangement and substrate are arranged in between the resilient legs. The filament arrangement and substrate are clamped in between the resilient leg portions, for example leaf springs, of the clamping means. The spring force of the resilient leg portions defines the clamping force. The portion of the clamping means extending over the lateral side of the substrate may serve as electrical contact to an external power source. By this an electrical contacting of the heater assembly may occur from a top or bottom of the heater assembly but also or only from a lateral side. This may simplify contacting of the heater assembly with electrical connectors being arranged along inner walls of a main housing of an aerosol generating system. A contacting may also be improved due to connectors being contactable to more than one side of the heater assembly.

According to a further aspect of the fluid permeable heater assembly according to the invention, the substrate comprises recesses for receiving the filament arrangement and the clamping means in the recesses. Recesses may improve a clamping and contacting of the filament arrangement, due to a localization of the contacting location of the clamping means on or in the substrate. Recesses may also aid in defining a contacting area, for example a position or size of a contact area. A recess may for example also limit or prohibit a displacement, for example sliding, of the clamping means from the substrate or on the filament arrangement during assembly or in the assembled state. Recesses may be provided in a surface of the substrate, preferably a top surface and a bottom surface of the substrate. Recesses may extend partly into or may extend entirely through the substrate. Recesses may for example be grooves, holes or slits.

According to an aspect of the fluid permeable heater assembly according to the invention, the clamping means are staple-like elements inserted into recesses of the substrate. A staple-like element is basically u-shaped having two legs and a bridge portion between the legs. Staple-like element are simple in manufacture at low cost. Staple-like elements may easily be assembled with a substrate, for example by a linear pushing action. Thereby, the legs of the staple-like elements may be inserted into holes or recesses in the substrate, while the filament arrangement is arranged between substrate and staple-like element. During assembly, the filament arrangement is not at risk to be displaced but clamped upon contact of clamping means and substrate. Staple-like elements allow for different clamping mechanisms or variations thereof. For example, for a form-fit closure the legs may be inserted into holes in the substrate, protruding ends of the legs may be bent on the bottom surface of substrate and provide additional fixation of the clamping means on the substrate. Also a fixation of the filament arrangement, as well as a surface for the electrical contact between filament and clamping means may be improved by simple means when using staple-like elements. In some preferred embodiments this is done by recesses and staple-like elements comprising corresponding but non-planar contact surfaces. Therein 'non-planar contact surfaces' is understood to also include contact surfaces, which consist of several partial contact surfaces, which partial surfaces may be flat but which are arranged at an angle to each other, such that the contact surface is non-planar.

An enlarged contact surface secures good electrical contact between filament and clamping means. Due to an additional structure in the contact surface, also a fixation of the filament arrangement may be improved. A pulling force onto the filament arrangement may be enhanced, improving the stability of the filament arrangement. A side of the staple-like element facing a recess in the substrate may have a non-planar form. This non-planar form may also be present on the side of the staple-like element to be contacted by a connector of a battery. Thus, also a contact area between clamping means and external connector may be enlarged and improved.

According to another aspect of the fluid permeable heater assembly according to the invention, the recesses are one or a combination of longitudinal recesses extending across at least a portion of a top surface of the substrate, individual through bores within the substrate or recesses in a circumference of the substrate. The different kind of recesses allow for a wide variety of clamping mechanisms and different embodiments and shapes of substrates and clamping means. Preferably, longitudinal recesses provided in the top surface of the substrate provide large contact areas. Longitudinal recesses may extend across a part or across the entire top surface of the substrate. Also a bottom surface may be provided with longitudinal recesses. Longitudinal recesses allow for flat heater assembly constructions due to a countersinking available for the clamping means in the recesses. Longitudinal recesses in a top surface of the substrate are especially preferred for clamping means that extend over a lateral side of the substrate and for clamping means having resilient leg portions that are entirely inserted into recess. In the latter embodiments, a clamping force acts inside the substrate. A longitudinal recess may also improve a clamping, where longitudinal edges of clamping means press against the top surface and the bottom surface of the substrate.

Bore holes or recesses in a circumference of a substrate allow a form fit closure of clamping means and substrate by providing a clamping means on the top surface and the bottom surface, however without adding material to a lateral side of the heater assembly. Thus, dimensional restrictions, for example of a main housing of a system will not be challenged by the heater assembly.

In some preferred embodiments of the fluid permeable heater assembly, the clamping means comprise resilient leg portions, which are arranged and clamped within the longitudinal recesses. In these embodiments, a clamping force acts in a lateral direction of the substrate and inside the substrate. The clamping means, especially the clamping action of the resilient leg portions arranged inside the recesses are well protected from influences of external elements, for example system elements arranged on top or below the heater assembly. Thus, a loosening effect of the clamping action, for example by a housing wall pressing against the clamping means may be avoided. Preferably, the clamping means are countersunk in the substrate, even more preferably substantially completely countersunk in the substrate except for a flat contact area. This facilitates the handling of the substrate during the manufacture of a very compact heater assembly.

A filament arrangement may extend partially or entirely over the opening in the substrate. Preferably, the filament arrangement covers about 50 percent to about 95 percent of the opening, for example covers between about 70 percent to about 90 percent of the opening in the substrate.

If the filament arrangement covers the entire opening, a maximal available area of a liquid surface or of an aerosol forming substrate arranged next to the heater is heated. Thus, high vaporization is achievable since heat is applied to a large surface. In addition, depending on the kind of aerosol forming substrate, for example a capillary material transporting liquid to the heater, a large heated area may support a homogeneous draining of the aerosol-forming substrate. At the same time, the area not covered by the substantially flat filament arrangement may contribute differently to the aerosol generation in terms of flow rate or droplet size. This may be beneficial in order to optimize the generation of an aerosol with predetermined characteristics in a repeatable manner. For example, if the filament arrangement does not cover the entire opening, vaporized liquid may more easily pass through the heater assembly in those regions not covered by the filament arrangement. By this, aerosol production may be supported.

Preferably, the substantially flat filament arrangement is in direct contact with the capillary material transporting liquid to the heater. This facilitates a continuous stream of liquid to the substantially flat filament arrangement for the generation of an aerosol. Preferably, the transport medium is homogeneous.

In some preferred embodiments of the fluid permeable heater assembly according to the invention, the filament arrangement comprises a plurality of filaments forming a mesh.

A mesh provides a stable and robust filament arrangement. It also provides an easy handling during manufacture, easier than for example an array of filaments arranged parallel to each other. In addition, an ability of the mesh to retain liquid between the filaments may be selected and varied, for example, by varying a type of weaving or a lattice structure. A mesh is robust in a structural sense: Thus, a mesh has excellent fail-safe properties due to the redundancy of available electrical paths. Even if one filament of the mesh is broken or incompletely contacted the heater may still be operated with little change of overall electrical a thermal performance of the filament arrangement.

In some preferred embodiments of the fluid permeable heater assembly according to the invention, the substrate is an electrically isolating, substantially flat, preferably discshaped element. A flat heater assembly is space saving and provides easy handling upon manufacture and assembly of a system.

According to another aspect of the invention, there is provided a method for assembling a mesh heater for an aerosol-generating system. The method comprises the steps of providing a substrate, providing an opening through the substrate and arranging electrically conductive filaments over the opening of the substrate. Further steps of the method are mechanically fixing the filaments to the substrate by clamping means, thus clamping the filaments to the substrate, and providing an electrical contact to the filaments through the clamping means.

According to an aspect of the method according to the invention, the method further comprises the step of providing recesses in the substrate and pushing the clamping means into the recesses. By such a pushing, clamping means may be applied to the prepared filament-substrate configuration by a linear movement. This enables to assemble a heater in one single clamping step. A pushing may be performed substantially perpendicular to the substrate or substantially parallel to the substrate. A pushing substantially perpendicular to the substrate relates to a pushing from above the substrate against the top surface. A substantially parallel pushing relates to sideway application of the clamping means from a lateral side of the substrate or to an application of the clamping means by sliding the clamping means on the filament-substrate configuration.

Preferably, the step of insertion of the clamping means creates a stretching force in the direction of the plane of the substantially flat filament arrangement. This advantageously stretches the substantially flat filament arrangement to a predetermined tension. This allows for an improved contact surface between the substantially flat filament arrangement and the substrate. Further, this allows for an improved contact surface between the substantially flat filament arrangement and the transport medium.

According to another aspect of the method according to the invention, a clamping force acts in a direction substantially perpendicular to a top surface of the substrate. Typical representatives of such embodiments are for example sandwich clamping means, where the filament arrangement and substrate is sandwiched between portions of the clamping means.

According to another aspect of the method according to the invention, a clamping force acts in a direction substantially lateral to a top surface and within the substrate. Representatives of such embodiments are for example clamping means, which are arranged within the substrate, preferably within a recess in the substrate provided for receiving the clamping means or that part of the clamping means provided for clamping. Another part of the clamping means provided for an electrical contacting of the clamping means is then arranged outside of the recess.

According to another aspect of the method according to the invention, the filament arrangement includes a first portion and second portions that form an integrated filament, wherein the second portions are provided on either end of the filament arrangement and the first portion is provided between the second portions. As used herein, "integrated" means that the first portion and the second portions form a single body that provides an electrical pathway from one second portion to the other second portion via the first portion.

In such a configuration, the second portions may be formed of a different material than the first portion or additionally or alternatively of the same material but provided in a different form. For example, where the filament arrangement comprises a mesh, the second portions may take the different form of having a higher density mesh than in the first portion. Alternatively, the filament arrangement may be formed of a two different materials in the first portion and the second portions, where the material forming the second portions is more malleable and more easily deformed than the material of the first portion. In this case, for example, the first portion may be formed of stainless steel and the second portion may be formed of copper. Alternatively, the second portions may be formed of a foil between which the first portion is provided such that the first portion and second portions form an integrated filament.

When the filament arrangement comprises first and second portions, the filament arrangement may be subjected to an additional step where the second portions are subjected to sufficient force such that they form a foil-like material. As used herein, a "foil-like" material is any material that is subject to a force that flattens the material while maintaining the integrated filament.

Further aspects and advantages of the method according to the invention are mentioned relating to the fluid permeable heater assembly and will not be repeated.

According to yet another aspect of the invention there is provided an aerosol generating system, preferably an electrically operated smoking system. The aerosol generating system comprises a storage portion comprising a housing for holding a liquid aerosol-forming substrate, wherein the housing has an open end. The system further comprises a fluid permeable heater assembly according to the invention and as described herein. The heater assembly is arranged next to the housing such that the filament arrangement of the fluid permeable heater assembly is arranged over the open end of the housing. The system further comprises a connector of a power source for electrically connecting the clamping means of the fluid permeable heater assembly to the power source.

Advantages and aspects of the aerosol generating system have been described relating to the heater assembly and will not be repeated. Due to the available variants of clamping means and according embodiments of heater assembly, a heater assembly may be adapted and manufactured, for example, to be suitable for existing main housings of such system. Such main housings may already include a cartridge containing an aerosol-forming substrate, electrical circuit, power source and electrical connectors for contacting the heater assembly.

A storage portion advantageously contains a capillary material. The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid to the heater. Alternatively, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic, The capillary material may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

Preferably, the capillary material is in contact with the electrically conductive filaments. The capillary material may extend into interstices between the filaments. The heater assembly may draw liquid aerosol-forming substrate into the interstices by capillary action. The capillary material may be in contact with the electrically conductive filaments over substantially the entire extent of the opening. The cartridge may contain two or more different capillary materials, wherein a first capillary material, in contact with the heater element, has a higher thermal decomposition temperature and a second capillary material, in contact with the first capillary material but not in contact with the heater element has a lower thermal decomposition temperature. The first capillary material effectively acts as a spacer separating the heater element from the second capillary material so that the second capillary material is not exposed to temperatures above its thermal decomposition temperature. As used herein, "thermal decomposition temperature" means the temperature at which a material begins to decompose and lose mass by generation of gaseous by products. The second capillary material may advantageously occupy a greater volume than the first capillary material and may hold more aerosol-forming substrate that the first capillary material. The second capillary material may have superior wicking performance to the first capillary material. The second capillary material may be cheaper than the first capillary material. The second capillary material may be polypropylene.

The first capillary material may separate the heater assembly from the second capillary material by a distance of at least 1.5 millimeter, and preferably between 1.5 millimeter and 2 millimeter in order to provide a sufficient temperature drop across the first capillary material.

The storage portion may be positioned on a first side of the electrically conductive filaments and an airflow channel positioned on an opposite side of the electrically conductive filaments to the liquid storage portion, such that air flow past the electrically conductive filaments entrains vaporised liquid aerosol-forming substrate.

The system may further comprise electric circuitry connected to the heater assembly and to an electrical power source, the electric circuitry configured to monitor the electrical resistance of the heater assembly or of one or more filaments of the heater assembly, and to control the supply of power to the heater assembly dependent on the electrical resistance of the heater assembly or the one or more filaments.

The electric circuitry may comprise a microprocessor, which may be a programmable microprocessor. The electric circuitry may comprise further electronic components. The electric circuitry may be configured to regulate a supply of power to the heater assembly. Power may be supplied to the heater assembly continuously following activation of the system or may be supplied intermittently, such as on a puff-by-puff basis.

The power may be supplied to the heater assembly in the form of pulses of electrical current.

The system advantageously comprises a power supply, typically a battery, within the main body of the housing. As an alternative, the power supply may be another form of charge storage device such as a capacitor. The power supply may have sufficient capacity to allow for the continuous generation of aerosol for a period of around six minutes. In another example, the power supply may have sufficient capacity to allow for a predetermined number or discrete activations of the heater assembly.

The invention is further described with regard to embodiments, which are illustrated by means of the following drawings, wherein:

FIGS. 7a and 7b show a heater assembly with staples as clamping means and details of parts of the cross section of the substrate;

FIG. 8 shows a further embodiment of a heater assembly with staples as clamping means;

FIG. 9 shows heater assemblies with mounted staples;

FIG. 10 shows a further embodiment of heater assembly with staples as clamping means;

In the figures, the same reference numerals are used for the same or similar elements.

Figure 1:
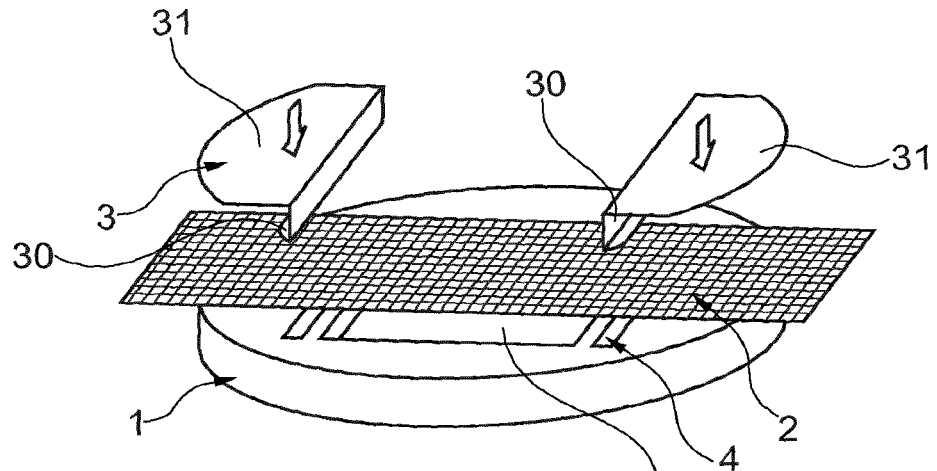
FIG. 1 shows an embodiment of a heater assembly.
Figure 2:
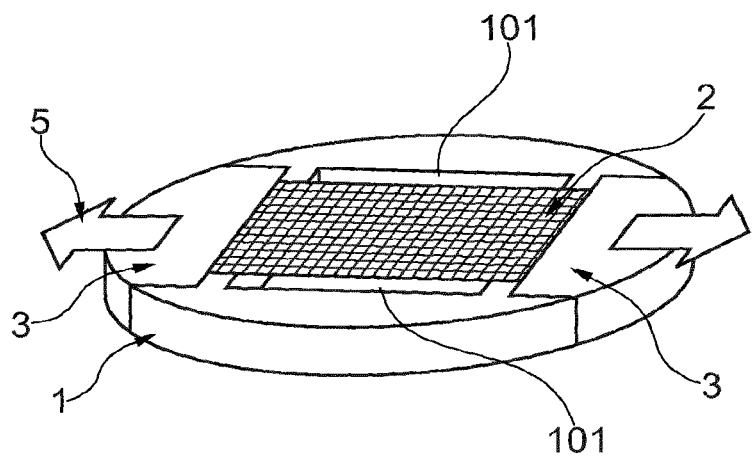
FIG. 2 shows the heater assembly of FIG. 1 in a mounted state.

In FIG. 1 and FIG. 2 a heater assembly including an electrically insulating substrate 1, a heater element and filament arrangement in the form of a mesh 2 and two clamps 3 for attaching the mesh to the substrate are shown. The substrate 1 has the form of a circular disc and comprises a centrally arranged opening 100. The substrate also comprises two slits 4 arranged parallel to each other and next to each side of the square-formed opening 100. The mesh 2 in the form of a band is arranged over the opening and over the slits 4. The width of the mesh is smaller than the width of the opening 100 such that on both lateral sides of the mesh an open portion 101 of the opening is formed, which open portions are not covered by the mesh. The two clamps 3 comprise a flat contact portion 31 to be arranged parallel to the top surface of the substrate. The contact portions 31 are for contacting the heating assembly by an electrical connector from a battery. The two clamps 3 also comprise a longitudinal folded clamping portion 30 for being inserted into the slits 4 in the substrate 1.

The clamps 3 may be folded from a piece of metal such as, for example, a stainless steel or copper sheet.

FIG. 2 shows the heater assembly in an assembled state, wherein the mesh 2 has been pushed into the slits 4 upon pushing the clamps 3 perpendicular to the top surface into the slits (pushing direction is indicated by arrows in FIG. 1). By the clamps 3 a pulling force 5 acting in a direction coplanar to the top surface of the substrate 1 acts on the mesh 2. Each of the clamps 3 causes a pulling force 5 acting in opposite direction. This pulling force 5 supports the planar arrangement of the mesh 2 and helps to stabilize the mesh in the plane of the substrate 1.

Figures 3A, 3B:
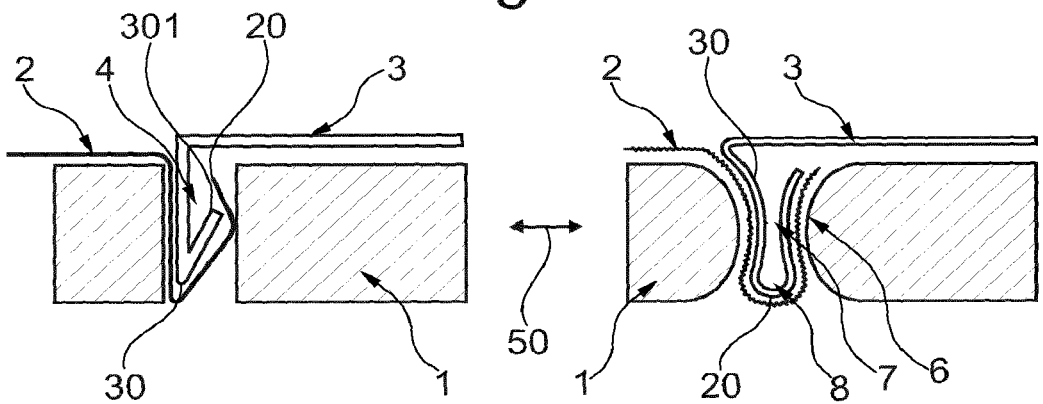
FIGS. 3a and 3b show details of clamping mechanisms.

FIG. 3a shows the detailed view of the inserted clamp 3 in slit 4. End portions 20 of the mesh 2 are pushed into the slits by the clamping portions 30 of the clamps and securely clamped in the slits. The folded clamp portions 30 execute a clamping force 50 onto the walls of the slits in a direction parallel to the top surface of the substrate and within the substrate. Edges 301 of the clamps 3 may act as barbs, additionally fixing the mesh in the slits and improve secure electrical contact of clamps 3 with mesh 2.

FIG. 3b shows an alternative embodiment of a folded clamping portion 30 of a clamp 3 inserted in a longitudinal slit 4. The slit has convex walls 6, which press the clamp at its narrowest folded part 7 of the inserted clamping portion 30. In this embodiment, the narrowest folded part 7 is in about half the height of the substrate 1. By this, the (larger) folded part 8 inserted deepest into the slit 4 is further prevented to leave the slit.

FIGS. 4a to 4d show embodiments of clamps 3, which clamp the substrate 1 on the top surface and on the bottom surface. Upper and lower clamping edges 9, 10 press into the top and bottom surface of the substrate 1. The mesh 2 is arranged between at least the upper clamping edge 9 and the top surface of the substrate. This upper edge 9 directs slightly into a backwards direction such as to have a more stable construction when pulling the mesh 2 against this backward direction.

The clamps 3 comprise a lateral portion 32 arranged at a lateral or circumferential side of the substrate 1. The lateral portion 32 of the clamps may further support a clamping and contacting of the mesh 2 by contacting the lateral side of the substrate 1.

Figure 4A:
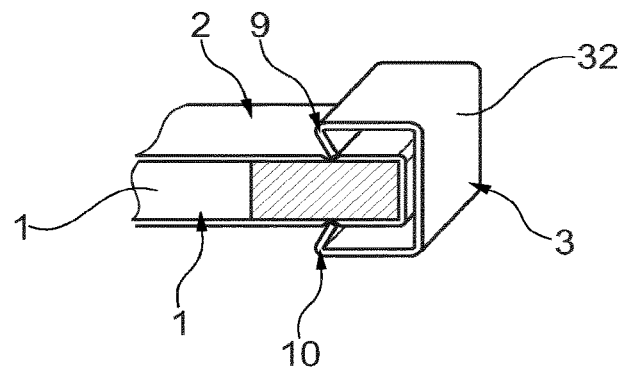
FIGS. 4a-4d show further clamping means and clamping mechanisms.
Figure 4B:
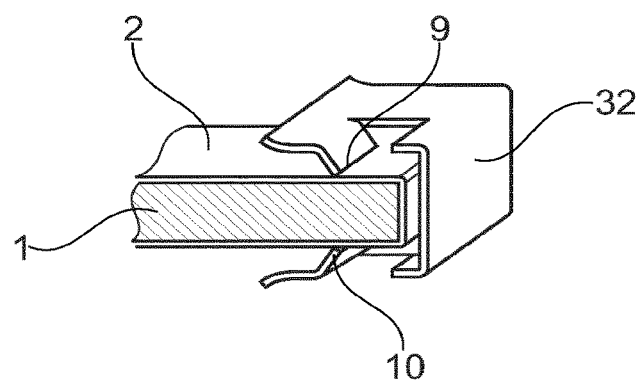

In FIGS. 4a and 4b the mesh 2 is guided around the circumference of the substrate 1 and is fixed to both sides of the substrate. The clamping edges 9, 10 of the clamp 3 in FIG. 4b do not extend along the entire longitudinal extension of the clamp. The edges are formed by cut outs of the clamp sheet bent to direct versus top or bottom surface, respectively, of the substrate 1.

Figure 4C:
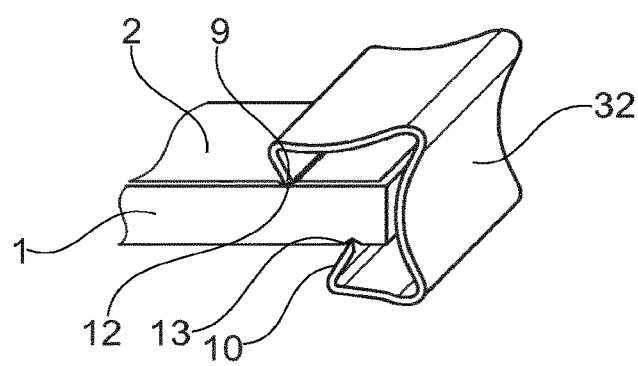

Side walls of the clamp 3 in FIG. 4c are smoothly bent altering the resiliency of the clamp. The top and bottom surface of the substrate 1 is provided with longitudinal recesses 12, 13 in the form of notches for receiving the clamp edges 9, 10, as well as the mesh 2 (upper recess 9 only in this embodiment).

Figure 4D:
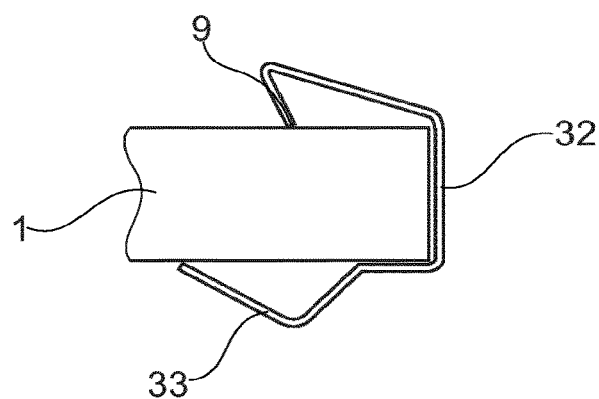

The lateral side 32 of the clamp 3 of FIG. 4d closely contacts the lateral side of the substrate as well as a part of the bottom surface of the substrate 1. On the bottom surface, the clamp forms a triangle 33 when seen from the side. The length of the triangle 33 may be adapted and varied to vary a clamping force of the clamp 3.

A heater assembly provided with clamps as shown in FIGS. 4a to 4d may be assembled by arranging the mesh 2 over the substrate 1 and by bending the clamps while assembling the heater. A pulling force on the mesh is then provided upon bending the clamps.

Figure 5A:
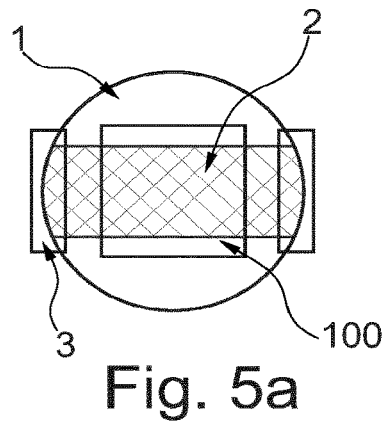
FIGS. 5a and 5b show top views of the heater assembly.
Figure 5B:
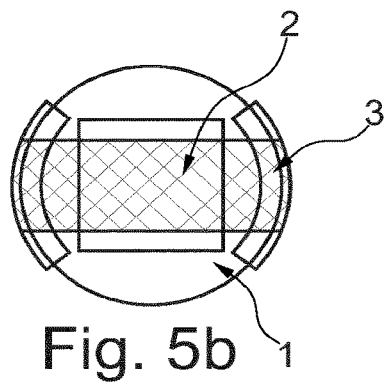

FIGS. 5a and 5b show top views of heater assemblies with clamps having longitudinal clamping portions, such as for example shown in the embodiments of FIGS. 4a to 4d and FIGS. 6a to 6c. The clamps 3 in FIG. 5a have a substantially rectangular form when seen from above or from below. Such clamps are simple to manufacture, for example by bending a rectangular piece of sheet material or wire. The clamps as shown in FIG. 5b have forms adapted to the form of a substrate. Thus, a circular substrate is provided with clamps adopting the circular form of the circumference of the substrate. Such a heater assembly is very compact and space saving also in lateral dimensions.

Figure 6A:
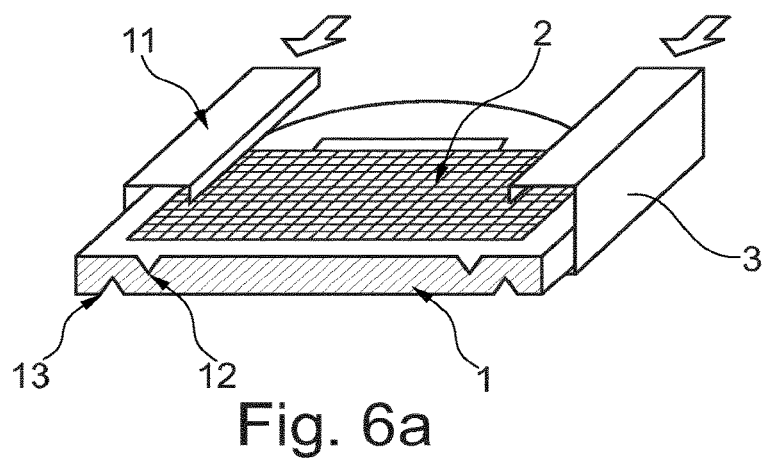
FIGS. 6a-6c show a heater assembly with sideways slidable clamping means (FIG. 6a); details of the clamping mechanism (FIG. 6b); and clamping means (FIG. 6c)
Figure 6B:
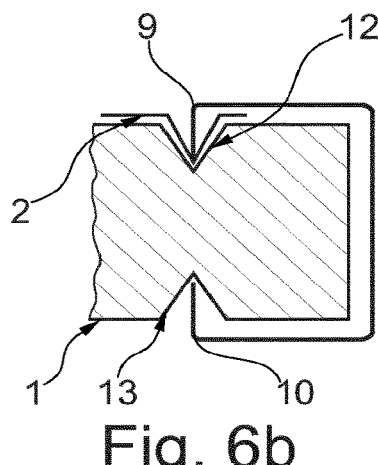
Figure 6C:
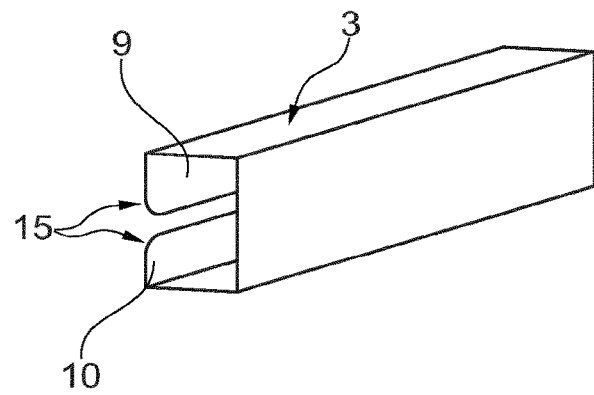

In FIGS. 6a to 6c a heater assembly and clips are shown, which clips may be slid onto the prepared substrate 1 and mesh 2 configuration. The substrate has longitudinal recesses 12, 13 in the form of notches in the top surface and in the bottom surface. The recesses 12, 13 are arranged parallel to each other, parallel to the opening 100 in the surface and extend across the entire surface of the substrate 1. The recesses 12, 13 facilitate the sideway sliding of the clips 3 onto the mesh-substrate configuration. Preferably, the mesh 2 is firmly stretched before sliding the clips 3 onto the substrate 1. To prevent the tearing of the mesh or a getting caught in the mesh upon sliding on, the edges 15 of the clip are rounded. This may be seen in FIG. 6c showing a pre-manufactured clip 3 as clamping means.

In FIGS. 7a, 7b, 8, and 10 clamping means 3 in the form of two staples and corresponding recesses 12 in the substrate 1 are shown. A mesh (not shown) is arranged over at least a portion of the opening 100 in the substrate. The staples are vertically inserted into recesses 12, 120, 122 in the substrate. In the mounted position, the bridges of the staples come to lie in the longitudinal recesses 12 provided in the top surface of the substrate 1. The legs have a length longer than the thickness of the substrate 1. The projecting leg ends are bent and countersunk in corresponding recesses 19 in the bottom surface of the substrate. With the legs bent around the substrate, the mesh 2 is securely clamped and contacted by the staple. In FIGS. 7a and 8, the four legs of the two staples are inserted into four recesses 121 arranged in the circumference of the disc-formed substrate. In FIG. 7a, the bridges of the staples have an embossed shape 17 in the form of a roof. Such a form may directly correspond to the form of connectors of a battery. The longitudinal recesses 12 in the substrate also have a corresponding roof-shaped form of the bottom of the recess 18 as may be seen in the cross sectional detailed view depicted in FIG. 7b.

In FIG. 8 the bridges of the staples have an engraved v-shaped form 20, which corresponds to a corresponding engraved v-shape form 21 of the recesses 12.

A stretching of the mesh is caused by the corresponding shapes 17, 18; 20, 21 of staple and recess 12.

FIG. 9 shows the two heating assemblies of FIG. 7a and FIG. 8 in the assemble state. Therein, the heating assembly as shown in FIG. 7a corresponds to the embodiment as shown on the bottom of FIG. 9 and FIG. 8 corresponds to the embodiment shown on top of FIG. 9.

FIG. 10 is a further variant of a heating assembly with staples as clamping means 3. The substrate is provided with two longitudinal recesses 12 for receiving the bridge portion of the staples. The substrate is also provided with one hole 122 at each end of the longitudinal recesses 12. The legs of the staples are pushed into the holes 122 and a mesh (not shown) is clamped and contacted between the recess 12 and the staple. The staples 3 may be attached to the substrate 1 by a form-fit between the legs of the staples and the holes 122. However, the bottom surface of the substrate may also be provided with recesses for receiving leg ends bent at the bottom of the substrate.

Figure 11A:
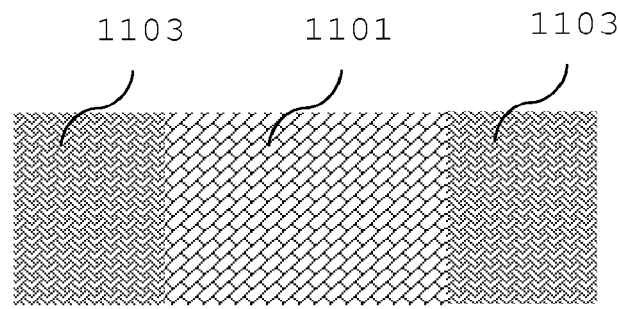
FIGS. 11a-11d show filament arrangements having first and second portions and methods for manufacturing integrated filaments.
Figure 11B:
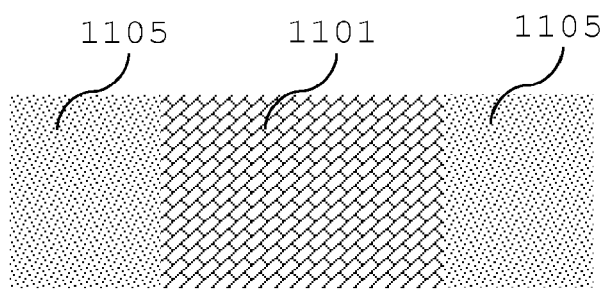
Figure 11C:
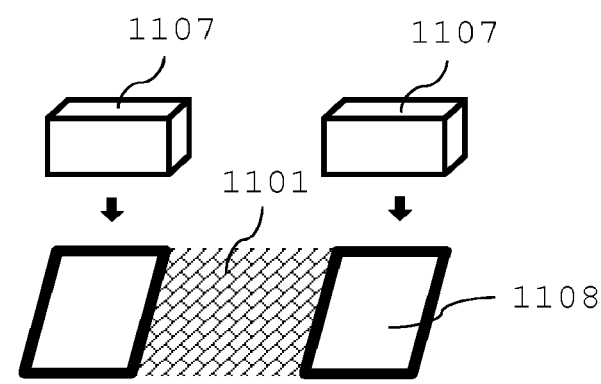
Figure 11D:
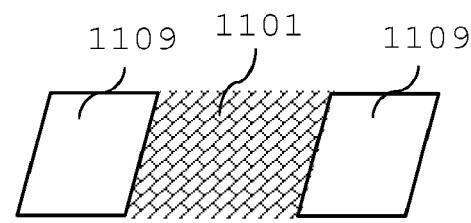

FIGS. 11a to 11d illustrate methods of providing an integrated filament having first and second portions. In FIG. 11a, the first portion is illustrated as a mesh 1101 and the second portions are illustrated as a higher density mesh 1103. For example, the first portion may comprise a lower density mesh than the second portions but both the first and second portions are formed of a single material, such as stainless steel. In FIG. 1ib, the first portion is illustrated as a mesh 1101 comprising a first material and the second portions 1105 are illustrated as end portions being formed of a second material other than the first material. Therein, the second material is more malleable than the first material. As an example, first portion 1101 may be stainless steel and the second portion 1105 may be copper. FIG. 11c illustrates subjecting the second portions 1108 to a force with pressing elements 1107 such that the second portions 1108 are deformed and are a foil-like material 1109 as illustrated in FIG. 11d.

After forming the resulting integrated filament including first 1101 and second portions 1103, 1105, 1109, the integrated filament may be affixed to a substrate using one of the methods described above by providing the second portions 1103, 1105, 1109 such that clamps 3 are electrically connected to the second portions.

Figure 12:
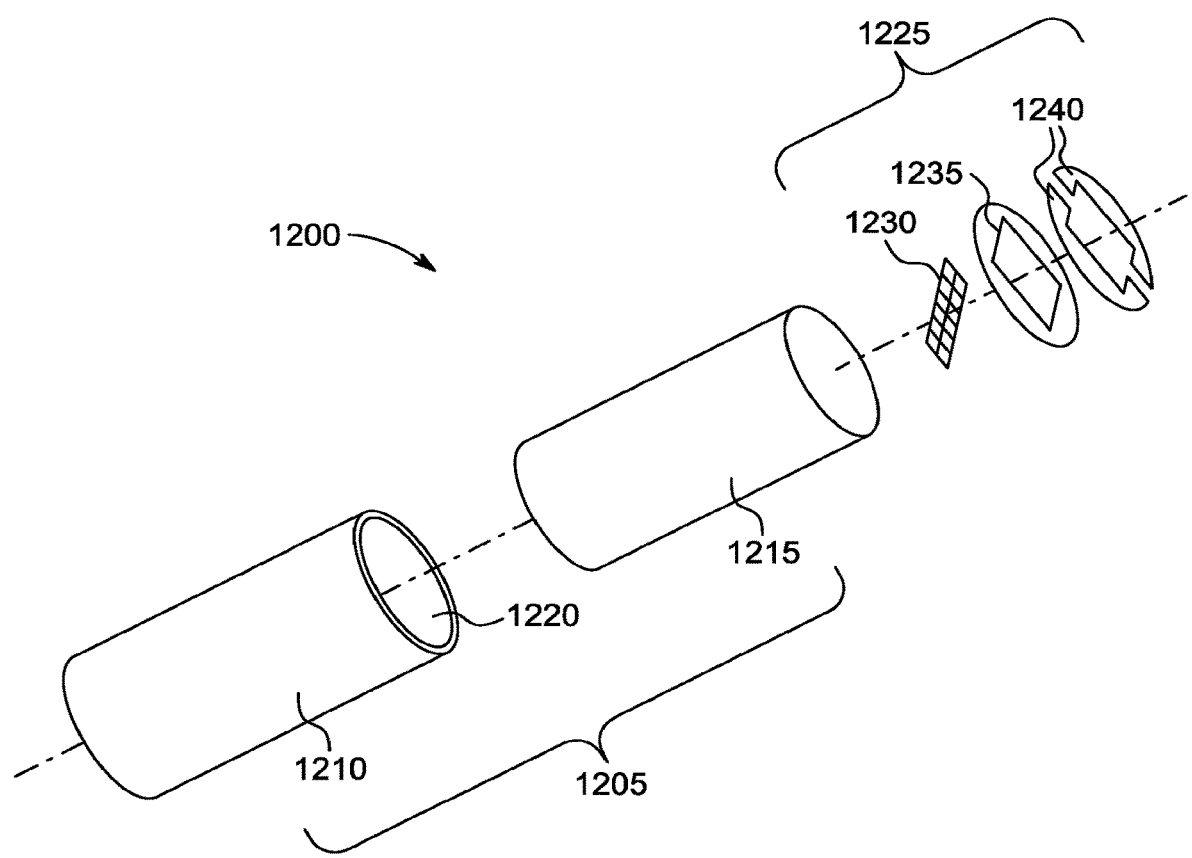
FIG. 12 shows an exploded view of an embodiment of an aerosol generating system including a storage portion and a fluid-permeable heater assembly.

In FIG. 12, an exploded view of an aerosol generating system 1200, preferably an electrically operated smoking system, is shown. The aerosol generating system 1200 comprises a liquid storage portion 1210 comprising a housing for holding a liquid aerosol-forming substrate 1215, wherein the housing has an open end 1220. The aerosol generating system 1200 further comprises a fluid-permeable heater assembly 1225 according to the invention and as described herein. The fluid-permeable heater assembly 1225 is arranged next to the housing such that the electrical heating element (filament arrangement 1230) of the fluid-permeable heater assembly 1225 is arranged over the open end of the housing. The aerosol generating system 1200 further comprises an electrically insulating substrate 1235 having a planar attachment face on which the filament arrangement 1230 is disposed in contact, and connectors (electrical contacts 1240) of a power source for applying electrical power to the filament arrangement 1230 of the fluid-permeable heater assembly 1225.

The invention has been described in more detail by means of the embodiments shown in the drawings. However, further embodiments of clamping mechanisms and corresponding clamping means and substrate forms may be envisaged. For example, a mesh may be attached to the substrate by screws. The screws then are electrically conductive and serve as electrical contacts for the filament arrangement and as connectors for a battery. There may also be a clipping engagement between the clamping means and the substrate in the form of, for example, a press button or snap fastener. Therein, a clamping means forms one part of the snap fastener and the substrate is provided with the corresponding other part of the snap fastener.

The invention claimed is:

1. A cartridge for an aerosol-generating system, the cartridge comprising:
   a liquid storage portion comprising a housing containing a liquid aerosol-forming substrate, the housing having an open end; and
   a heater assembly comprising:
      an electrical heating element configured to heat the liquid aerosol-forming substrate to form an aerosol, the electrical heating element including a planar filament arrangement having one or more electrically conductive filaments,
      an electrically insulating substrate having a planar attachment face, the filament arrangement being disposed on the planar attachment face, and
      clamping elements mechanically fixing the filament arrangement to the electrically insulating substrate and applying a pulling force onto the filament arrangement,
   wherein at least a portion of the heater assembly is fluid-permeable, and
   wherein the heater assembly is arranged over the open end of the housing.

2. The cartridge according to claim 1, wherein the clamping elements are configured to apply a pulling force into a direction coplanar to the planar attachment face.

3. The cartridge according to claim 1, where the clamping elements are configured to apply opposite pulling forces.

4. The cartridge according to claim 1,
   wherein the clamping elements are electrically conductive and serve as electrical contacts configured to provide an electrical current through the filament arrangement.

5. The cartridge according to claim 1, wherein the one or more electrically conductive filaments has a flat cross-section.

6. The cartridge according to claim 1, wherein the electrically insulating substrate further comprises an open-pored ceramic material.

7. The cartridge according to claim 1,
   further comprising a capillary material,
   wherein the filament arrangement is disposed in physical contact with the capillary material.

8. The cartridge according to claim 1, wherein the filament arrangement comprises a woven mesh.

9. The cartridge according to claim 1, wherein the electrically insulating substrate has an opening.

10. The cartridge according to claim 9, wherein the planar attachment face includes the opening.

11. The cartridge according to claim 9, wherein the opening of the electrically insulating substrate extends through the electrically insulating substrate.

12. The cartridge according to claim 9, wherein the filament arrangement extends at least partially over the opening of the electrically insulating substrate.

13. The cartridge according to claim 1,
   wherein the electrically insulating substrate has holes formed therein, and
   wherein the clamping elements extend into the holes.

14. The cartridge according to claim 1,
   wherein the electrically insulating substrate has recesses formed therein, and
   wherein the clamping elements extend into the recesses.

15. The cartridge according to claim 1,
   wherein the electrically insulating substrate has holes formed therein, and
   wherein the holes extend partly through the electrically insulating substrate.

16. The cartridge according to claim 1, wherein the filament arrangement has a first portion and second portions, the second portions provided on either end of the first portion of the filament arrangement, the first portion and the second portions being an integrated electrical pathway.

17. The cartridge according to claim 1,
   wherein the filament arrangement has a first portion and second portions, the second portions provided on either end of the first portion of the filament arrangement, the first portion and the second portions are formed of a single material,
   wherein the first portion of the filament arrangement comprises a mesh having a first density,
   wherein the second portions of the filament arrangement comprise the mesh having a second density, and
   wherein the second density is greater than the first density.

18. The cartridge according to claim 17, wherein the mesh is a woven mesh.

19. The cartridge according to claim 1, wherein the electrically insulating substrate has two planar attachment faces.

20. The cartridge according to claim 1, wherein the liquid aerosol-forming substrate is disposed on a first side of the planar filament arrangement and an airflow channel is disposed on an opposite side of the planar filament arrangement.

\* \* \* \* \*